United States Patent [19]

Nakano

[11] Patent Number: 5,929,047
[45] Date of Patent: Jul. 27, 1999

[54] ANTI-VIRAL AGENT PREPARED BY BASIC AND ACIDIC EXTRACTION OF MANGRAVES

[75] Inventor: Masatoshi Nakano, Aichi, Japan

[73] Assignee: Mitsui Norin Co., Ltd., Tokyo, Japan

[21] Appl. No.: 08/809,964

[22] PCT Filed: Jul. 31, 1996

[86] PCT No.: PCT/JP96/02155

§ 371 Date: Jun. 3, 1997

§ 102(e) Date: Jun. 3, 1997

[87] PCT Pub. No.: WO97/04791

PCT Pub. Date: Feb. 13, 1997

[30] Foreign Application Priority Data

Jul. 31, 1995 [JP] Japan .................................. 7-214232

[51] Int. Cl.⁶ ...................... A61K 31/70; A61K 31/715; C07H 1/08; C07H 3/04
[52] U.S. Cl. .......................... 514/53; 514/54; 536/123.1; 536/123.13; 536/124
[58] Field of Search ............................ 536/123.1, 123.13, 536/124; 514/53, 54

[56] References Cited

U.S. PATENT DOCUMENTS

4,985,249  1/1991  Sakagami et al. .

FOREIGN PATENT DOCUMENTS

| | | |
|---|---|---|
| 64-6218 | 1/1989 | Japan . |
| 1-238532 | 9/1989 | Japan . |
| 2-172922 | 7/1990 | Japan . |
| 4-128237 | 4/1992 | Japan . |
| 5-271088 | 10/1993 | Japan . |
| 7-194640 | 8/1995 | Japan . |
| WO 92/06106 | 4/1992 | WIPO . |

OTHER PUBLICATIONS

Patent Abstracts of Japan of JP 05–271061 published Oct. 19, 1993.
Patent Abstracts of Japan of JP 05–271062 published Oct. 19, 1993.
Patent Abstracts of Japan of JP 05–271090 published Oct. 19, 1993.
Patent Abstracts of Japan of JP 05–286866 published Nov. 2, 1993.
Patent Abstracts of Japan of JP 06–128121 published May 10, 1994.
Patent Abstracts of Japan of JP 06–199696 published Jul. 19, 1994.
Patent Abstracts of Japan of JP 06–199697 published Jul. 19, 1994.
Patent Abstracts of Japan of JP 07–039339 published Feb. 10, 1995.
Patent Abstracts of Japan of JP 08–151329 published Jun. 11, 1996.
Patent Abstracts of Japan, vol. 95, No. 5, Jun. 30, 1995 of JP 07 039339 A (Nippon Ruibosuteii Honsha KK), Feb. 10, 1995.
Patent Abstracts of Japan, vol. 18, No. 46 (C–1157), Jan. 25, 1994 of JP 05 271062 A (Ruibosuteii Japan KK et al), Oct. 19, 1993.
Patent Abstracts of Japan, vol. 18, No. 46 (C–1157), Jan. 25, 1994 of JP 05 271063 A (Ruibosuteii Japan KK et al) Oct. 19, 1993.
M. Premnathan et al, "A Survey of Some Indian Marine Plants for Antiviral Activity", Botanica Marina, vol. 35, 1992, pp. 321–324.
K. Komatsu et al, "Inhibitory effects of Rooibos tea, *Aspalathus linealis*, on X–ray–induced C3H10T1/2 cell transformation", Cancer Letters vol. 77, 1994, pp. 33–38.
D. Takemoto et al, "Purification and characterization of a cytostatic factor with anti–viral activity from the bitter melon", Preparative Biochemistry, vol. 13, No. 4, 1983, pp. 371–393.

*Primary Examiner*—Gary L. Kunz
*Attorney, Agent, or Firm*—Frishauf, Holtz, Goodman, Langer & Chick, P.C.

[57] ABSTRACT

An anti-viral agent comprising as the effective component, an alkali extract of mangroves, *Momordica charantia,* and *Aspalathus linearis* belonging to Leguminosae family. The effective component is essentially consists of acidic polysaccharides and shows an antioxidant activity and free radical (reactive oxygen species)-scavenging activity.

The agent is effective against retrovirus such as human immuno deficiency virus (HIV), with no side-effects on human and/or animals.

19 Claims, No Drawings

ANTI-VIRAL AGENT PREPARED BY BASIC AND ACIDIC EXTRACTION OF MANGRAVES

FIELD OF THE INVENTION

The present invention relates to an anti-viral agent comprising acidic polysaccharides having an antioxidant activity and a free radical (reactive oxygen species)-scavenging activity extracted as an active component from pecan nut, pine cone Eucommia plant(bark), Eucommia tea(leaf and twigs) *Aspalathus linearis* belonging to the Leguminosae family, mangroves, and *Momordica charantia,* and which are effective against retroviruses such as human immuno deficiency virus (HIV), with no side-effects on human and/or animals, easy to ingest daily and have preventive activity against virus infection, and also relates to a process of manufacturing the same.

BACK GROUND OF THE INVENTION

Numerous anti-viral agents are known heretofore.

However, most of the anti-viral agents developed so far are costly, and have weak efficacy and usually have side-effects which might have been severe and serious.

There are many diseases caused by viruses such as influenza, hepatitis, measles, Japanese encephalitis, human T-cell leukemia, and AIDS, and unfortunately though there are few effective chemotherapy treatments which show a definite effectiveness against these kinds of viral diseases, and in particular there is no medicine which is sufficiently effective against retroviruses which cause human T-cell leukemia or AIDS, without side-effects. Moreover, there are no anti-viral agents known which can be ingestable daily like food and drink and have preventative effects with no side-effects.

Recently a hot water extract of *Aspalathus linearis* is recognized effective against virus but the reason for its effectiveness is still unknown and research for searching for a stronger anti virus agent has been continued.

The purpose of the present invention is to resolve the above mentioned problems and to provide an anti-viral agent having an anti-oxidant activity and free radical-scavenging activity which is effective against retroviruses and has a protective activity without side-effects; and to provide a process of manufacturing such anti-viral agent.

DESCRIPTION OF THE INVENTION

The inventors of this application undertook an extensive research in order to resolve the above mentioned problems and discovered that acidic polysaccharides obtained from mangrove, *Momordica charantia L.,* and *Aspalathus linearis,* have a strong anti-viral activity, an anti-oxidant activity and a free radical-scavenging activity, and they have no side-effects and are safe on human and/or animals, and thus the present invention was developed.

Acidic polysaccharides stated above can be obtained by an alkaline extract method of mangrove, *Momordica charantia L.,* and *Aspalathus linearis,* which contain an uronic acid, neutral sugars and reducing sugars.

And further by hydrolyzing the acidic polysaccharides obtained from the plants in an acid, an anti-viral agent containing disaccharides and trisaccharides is produced.

THE BEST MODE OF THE INVENTION

Preferable plants for extraction are mangrove, *Momordica charantia L.,* and *Aspalathus linearis* belonging to the Leguminosae family, etc.

A further research on acidic polysaccharides obtained from plants shows that the polysaccharides containing uronic acids, neutral sugars and reducing sugars have a very strong antioxidant activity and a free radical scavenging activity and an anti viral effects. The acidic polysaccharides having these features are obtained by an alkaline hot water extraction method.

The effective ingredients of this invention is obtained by extracting the respective plants in hot water, such as mangrove, *Momordica charantia L.,* and *Aspalathus linearis* belonging to the Leguminosae family, etc. and then by adding an alkaline solution to the residues from the first hot water extraction, the alkaline extracts are obtained. Also the effective components can be obtained without extracting the plants in hot water but only by extracting the plants in the alkaline solution directly.

In the hot water extraction process, the amount of water may be 10 to 100 times of the weight of *Aspalathus linearis* and preferably the plants were extracted at 70–100 ° C. for 30 minutes to 4 hours. After extraction in hot water, the residue plants may be dried under the sunlight or indoors for 1–3 days.

Examples of the alkaline solution includes a sodium hydroxide, a potassium hydroxide, an ammonium hydroxide (ammonia solution), a sodium bicarbonate, a sodium carbonate, etc., and a known method of extraction such as a heat extraction is used for alkaline extraction. An isolation of extracted solution may be carried out by known methods such as a filtration, a decantation, or a centrifugation.

Ethanol, acetone, etc., may be used as extraction solvents and the extract can be dried up by known methods such as a freeze-dry method, or a spray-dry method.

To isolate and to purify the acidic polysaccharides from the extract, ethanol is added to the crude alkaline extract to obtain an ethanol concentration of 25%–75% (v/v) and kept standing for 30 minutes to one night at 4 ° C., then the precipitate is centrifuged and dried to finally obtain the acidic polysaccharides having an anti-oxidative and a free radical-scavenging activity.

The acidic polysaccharides having anti-oxidative and free radical-scavenging activity contain 21% of uronic acid, 49% of neutral sugar, and 26% of reducing sugar in case of *Aspalathus linearis,* 13% of uronic acid, 17% of neutral sugar, and 6% of reducing sugar in case of Eucommia elmoides, and 25% of uronic acid, 38% of neutral sugar, and 31% of reducing sugar in case of pine seed shells.

The acidic polysaccharides are further hydrolyzed in an acid at 75° C.–150° C. for 3 hours to 24 hours, and an oligosaccharide containing disaccharides and trisaccharides are obtained. The concentration of the acid may be in the range of 0.5N to 3N. Examples of the acid are hydrochloric acid, sulfuric acid, nitric acid, trifluoroacetic acid and they are used as known methods for acid hydrolysis.

The effective ingredients of the extract may be mixed with a suitable carrier such as an excipient, a binding agent, or a diluent, and provided in the various forms, such as granules, powder, hard capsules, soft capsules, an ointment, a syrup, suppositories, an injection; in any oral or non-oral form, and also may be ingested directly in the form of solution, powder, granules, tablets, emulsion, jelly, etc., or any other form, as a condensed solution or alternatively may be used by mixed with other foods or beverages.

The dosage of the invention depends on the symptom and the status of disease, in case of liquid form, it is preferable to take 2 to 500 ml per day of 1 to 1000 mg/l concentration and in case of powder form, 0.1 to 5 g/day is preferable.

An acute toxicity test of the acidic polysaccharides of this invention using rats was conducted. No animals died in the toxicity test and no abnormal results were observed in the biochemical and pathological examination.

EXAMPLE 1

Aspalathus linearis leaves containing sprigs were cut into 5 mm length, and subjected to a rolling process, an enzyme fermentation, and to drying process under sunlight to obtain dried leaves. 3 g of the dried leaves(with stem) were extracted with 100 ml of 85° C. hot water for 3 hours, and the residue leaves after hot water extraction were dried in indoor. 50 ml of 1% sodium hydroxide solution was poured into the residue leaves, and were shaked vigorously at 45° C. for 3 hours. A crude alkaline extract solution was obtained with a filtration through one layer of gauze. The alkaline extract was freeze-dried and the dried powder of Aspalathus linearis was obtained. The powder was dissolved in water, and a 0.1 M sodium acetate was added into the dissolved extract. Then ethanol was added into the extract to obtain a 25%–75% of concentration, and kept standing for more than 30 minutes at 4° C. Acidic polysaccharides having antioxidative activity was obtained by centrifuging the precipitate which contained 22.5% of uronic acid, 50.5% of neutral sugar, and 26.5% of reducing sugar.

The antioxidative activity of the acidic polysaccharide was measured by autooxidation of linoleic acid at 30° C., and the rate of autooxidation after 3 weeks (the antioxidative activity) was 5% against the water (control); namely in the case of water the rate of autooxidation was 100%. Moreover, when the activity was expressed as the time reaching to 50% autooxidation of linoleic acid, the acidic polysaccharides from Aspalathus linearis showed extremely low autooxidation level (below 5% autooxidation) even after 60 days. In this type of expression, antioxidative activity of the control (water) was 2 weeks. Furthermore, when the free radical-scavenging activity was measured by the method of electron spin resonance, the activity of the acidic polysaccharides was $4.7 \times 10^3$ units/g which is remarkably high activity.

EXAMPLE 2

The acidic polysaccharides obtained in Example 1 were applied to cultured MDCK cells or MA104 cells. Immediately after the addition of the acidic polysaccharides, MDCK cells were infected with influenza virus, and MA104 cells were infected with herpes virus, and then their respective plaque formation was examined.

In the case of influenza virus the plaque formation was almost completely inhibited by 0.1 mg/ml concentration of the acidic polysaccharides, and in the case of herpes virus the plaque formation was inhibited more than 90% at the concentration of 1 μg/ml of the acidic polysaccharides.

EXAMPLE 3

The acidic polysaccharides in Example 1 were applied to MT-4cells ($2.5 \times 10^4$ cells/well) which were sterilized and infected with HIV. After culturing the cells for 5 days at 37° C. the number of viable cells was measured.

The anti-viral (anti-HIV) activity was expressed as the concentration of the acidic polysaccharides showing 50% protection against HIV-induced cytopathogenicity. The $EC_{50}$ (50% effective concentration) was 15 μg/ml.

EXAMPLE 4

Instead of the Aspalathus linearis leaves in the Example 1, pine seeds(including shells) were extracted according to the process explained in the Example 1 and the acidic polysaccharides were obtained.

The obtained acidic polysaccharides contain 17% of uronic acid, 47% of neutral sugar, and 12% of reducing sugar.

The acidic polysaccharides were applied to MT-4cells ($2.5 \times 10^4$ cells/well) which were sterilized and infected with HIV. After culturing the cells for 5 days at 37° C. the number of viable cells was measured.

The anti-viral (anti-HIV) activity was expressed as the concentration of the acidic polysaccharide showing 50% protection against HIV-induced cytopathogenicity. The $EC_{50}$ (50% effective concentration) of the acidic polysaccharide was 150 μg/ml.

Furthermore, when the free radical-scavenging activity was measured by the method of electron spin resonance (ESR), the activity of the acidic polysaccharides was $3.4 \times 10^3$ units/g which is remarkably high activity.

EXAMPLE 5

Instead of the Aspalathus linearis leaves in the example 1, Eucommia plant(bark), and Eucommia tea(leaf and twigs) were extracted according to the process explained in the Example 1 and the acidic polysaccharides were obtained.

The obtained acidic polysaccharides contain 13% of uronic acid, 25% of neutral sugar, and 5.6% of reducing sugar.

The acidic polysaccharides were applied to MT-4cells ($2.5 - 10^4$ cells/well) which were sterilized and infected with HIV. After culturing the cells for 5 days at 37° C. the number of viable cells was measured.

The anti-viral (anti-HIV) activity was expressed as the concentration of the acidic polysaccharide showing 50% protection against HIV-induced cytopathogenicity. The $EC_{50}$ (50% effective concentration) of the acidic polysaccharide was 124 μg/ml.

The antioxidative activity of the acidic polysaccharide obtained from the Eucommia plant(bark), and Eucommia tea(leaf and twigs) expressed by the time when the autooxidation reaches 50% was 60 days, which is considered to be very high.

EXAMPLE 6

The polysaccharides obtained in the Example 1 were further hydrolyzed with 1N HCl at 75° C. for 4 hours and with 3N HCl at 100° C. for 13 hours and the precipitate and the supernatant were obtained which were applied to MT-4cells ($2.5 - 10^4$ cells/well) which were sterilized and infected with HIV. After culturing the cells for 5 days at 37° C. the number of viable cells was measured.

The anti-viral (anti-HIV) activity was expressed as the concentration of the acidic polysaccharide showing 50% protection against HIV-induced cytopathogenicity. The $EC_{50}$ (50% effective concentration) of the acidic polysaccharide hydrolyzed with 1N HCl at 75° C. for 3 hours and with 3N HCl at 100° C. for 13 hours is shown in Table 1. Both the supernatants obtained by the acid hydrolysis described above were mainly a mixture of disaccharides and of trisaccharides.

TABLE 1

Anti-HIV Activity of Acidic Polysaccharides Hydrolyzed with HCl

| | Anti-HIV activity (concentration of 50% protection) | |
|---|---|---|
| | Supernatant ($\mu$g/ml) | Precipitate ($\mu$g/ml) |
| 1N hydrochloric acid at 75° C. | 334.0 | 25.6 |
| 3N hydrochloric acid at 100° C. | 35.4 | 24.5 |

EXAMPLE 7

Sugar composition of the acidic polysaccharides obtained by Example 1 with alcohol precipitation were analyzed by 2-aminopyridine method using High HPLC.

Few amino acids was found, and the most of the composition comprises neutral sugars, most of which was glucose and 20% of mannose was measured. However, an uronic acid was not detected by this measuring method. 1 g of dried powder contains 12.4% of uronic acid, 24.4% of neutral sugars, 13.1% of reducing sugars. The results of the analysis shows that 0.775 of glucose, 0.200 of mannose, 0.125 of galactose, 0.133 of xylose, fucose (not detected), and 0.058 of galactosamine. (unit is expressed as $\mu$mol/mg).

EXAMPLE 8

The alkaline extract(a crude extract) prepared in the Example 1 was dissolved in distilled water, and an ethanol was added into the aliquot to bring to 25% concentration, and kept standing for 30 minutes at 4° C. The aliquot was centrifuged at 3000 rpm for 20 minutes and the precipitate was designated as 25P. The supernatant was used for the further fractionation by 100% ethanol; namely ethanol was further added into the supernatant to bring to 50% concentration, and centrifuged as above, and the precipitate was designated as 50P. The supernatant was used for the further fractionation by 100% ethanol; namely ethanol was further added into the supernatant to bring to 75% concentration, and centrifuged as above, and the precipitate was designated as 75P. The anti-HIV activity of each fraction obtained as above is shown in Table 2.

TABLE 2

Anti-HIV activity of Alcohol Precipitate

| | Anti-HIV activity ($EC_{50}$) ($\mu$g/ml) |
|---|---|
| 25P | 119.0 |
| 50P | 15.0 |
| 75P | 3.7 |

EXAMPLE 9

Ten one month old kittens were divided into two groups; one is control group which was given no acidic polysaccharides with foods and the other is an experimental group which was given 2 mg of the acidic polysaccharides obtained from the plants per day with foods for one month, and every kitten was injected several times with 0.5 ml of cat AIDS(feline immuno deficiency virus positive) blood. After the injection of the blood, the kittens were observed for the next two months. An antibody value of the AIDS virus was inspected.

20% of the experimental group was infected with AIDS and 100% of the control group was infected.

EXAMPLE 10

5 to 8 year old cats infected with cat AIDS(feline immuno deficiency) and feline infectious leukemia were fed with foods containing 2 mg/day of the acidic polysaccharides for 3 to 6 months to observe the improvements of the symptoms.

Instead of mixing the acidic polysaccharides with foods, the alkaline extract obtained in the Example 4 was injected every other day intramuscularly with 0.5 ml as 2 mg/kg weight. The experiment was conducted on 5 cats for each case.

The results show that 60% of the group ingesting the acidic polysaccharides with foods, symptoms were improved, but no improvement in symptoms was observed in the group ingesting no acidic polysaccharides with foods. 80% of the group injected with the alkaline extract was improved in symptoms.

POSSIBLE APPLICATION

The present invention provides an anti-viral agent with a preventive effect against new viral infection against human and animals, and shows a marked effect of retroviruses and has no side-effects on humans and animals and effective components can be ingested orally with daily foods.

I claim:

1. An anit-viral composition comprising disaccharides and trisaccharides obtained by a process comprising:

(a) extracting leaves of a mangrove, *Momordica charantia L.*, or *Aspalathus linearis* belonging to the Leguminosae family with hot water at a temperature of 70 to 100° C. for 30 minutes to 4 hours to obtain residue leaves, (b) extracting the residue leaves from step (a) with an alkaline solution to form a crude alkaline extract, (c) adding to said crude alkaline extract of step (b) an organic extraction solvent at a concentration of 25–75% (v/v) to obtain acidic polysaccharides containing an uronic acid, a neutral sugar and a reducing sugar, and (d) hydrolyzing the acidic polysaccharides from step (c) at a temperature of 75 to 150° C. for 3 to 24 hours with an acid having a concentration of 0.5 to 3N.

2. The anti-viral composition of claim 1, wherein the acidic polysaccharides have an anti-oxidative activity and a free radical-scavenging activity.

3. The anti-viral composition of claim 1, wherein the alkaline solution contains a compound selected from the group consisting of sodium hydroxide, potassium hydroxide, ammonium hydroxide, sodium bicarbonate and sodium carbonate.

4. The anti-viral composition of claim 3, wherein the alkaline solution is 1% sodium hydroxide.

5. The anti-viral composition of claim 1, wherein the alkaline extraction is carried out on *Aspalathus linearis* and the acidic polysaccharides contain the following components: 2% uronic acid, 49% neutral sugar and 26% reducing sugar.

6. The anti-viral composition of claim 1, wherein the acid is selected from the group consisting of hydrochloric acid, sulfuric acid, nitric acid and trifluoroacetic acid.

7. The anti-viral composition of claim 1, which further comprises a carrier selected from the group consisting of an excipient, a binding agent and a diluent.

8. The anti-viral composition of claim 7, which is in a form selected from the group consisting of granules, a powder, a capsule, an ointment, a tablet, an emulsion, a solution and a jelly.

9. The anti-viral composition of claim 8, which is in a liquid form and is in a dose of 2 to 500 ml per day of a 1 to 1000 mg/l concentration.

10. The anti-viral composition of claim 8, which is in a powder form and is in a dose of 0.1 to 5 g/day.

11. The anti-viral composition of claim 1, wherein the acidic polysaccharides have a free-radical scavenging activity of $4.7 \times 10^3$ units/g, as measured by the electron spin resonance method.

12. A process of producing an anti-viral composition comprising:
(a) extracting acidic polysaccharides from leaves of a mangrove, *Momordica charantia L.,* or *Aspalathus linearis* belonging to the Leguminosae family by with hot water at a temperature of 70 to 100° C. for 30 minutes to 4 hours to obtain residue leaves.
(b) extracting the residue leaves from step (a) with an alkaline solution to form a crude alkaline extract,
(c) adding to said crude alkaline extract of step (b) an organic extraction solvent of a concentration of 25–75% (v/v) to obtain acidic polysaccharides containing an uronic acid, a neutral sugar and a reducing sugar, and
(d) hydrolyzing the acidic polysaccharides from step (c) at a temperature of 75 to 150° C. for 3 to 24 hours with an acid having a concentration of 0.5 to 3N.

13. The process of producing an anti-viral composition of claim 12, wherein the alkaline solution contains a compound selected from the group consisting of sodium hydroxide, potassium hydroxide, ammonium hydroxide, sodium bicarbonate and sodium carbonate.

14. The process of producing an anti-viral composition of claim 13, wherein the alkaline solution is 1% sodium hydroxide.

15. The process of producing an anti-viral composition of claim 12, wherein the acid is selected from the group consisting of hydrochloric acid, sulfuric acid, nitric acid and trifluoroacetic acid.

16. The process of producing an anti-viral composition of claim 12, wherein step (a) of the process is carried out on the *Aspalathus linearis* with water in an amount of 10 to 100 times the weight of the *Aspalathus linearis*.

17. The process of producing an anti-viral composition of claim 12, whereing the organic extraction solvent is ethanol.

18. The process of producing an anti-viral composition of claim 12, wherein the organic extraction solvent is acetone.

19. The process of producing and anti-viral composition of claim 17, which further comprises separating a precipitate after step (c) by carrying out centrifugation.

* * * * *